United States Patent [19]

Bowden

[11] 4,048,180
[45] Sept. 13, 1977

[54] PYRIDYL-TETRAHYDROPYRANS AND PROCESS FOR PREPARING SAME

[75] Inventor: Roy Dennis Bowden, Runcorn, England

[73] Assignee: Imperial Chemical Industries Limited, London, England

[21] Appl. No.: 174,522

[22] Filed: Aug. 24, 1971

Related U.S. Application Data

[62] Division of Ser. No. 804,993, March 6, 1969, Pat. No. 3,651,071.

[30] Foreign Application Priority Data

Mar. 18, 1968 United Kingdom .............. 13008/68
Dec. 20, 1968 United Kingdom .............. 60714/68
Dec. 20, 1968 United Kingdom .............. 60715/68
Dec. 20, 1968 United Kingdom .............. 60716/68

[51] Int. Cl.$^2$ ........................................... C07D 405/04
[52] U.S. Cl. ........................... 260/297 R; 260/293.69; 260/294.8 D; 260/296 D
[58] Field of Search .................... 260/294.8 G, 297 R, 260/293.69, 345.1

[56] References Cited

U.S. PATENT DOCUMENTS 3,306,905  2/1967  Hall et al. ..................... 260/290 P
3,577,424  5/1971  McGill et al. .................. 260/297 R Primary Examiner—Alan L. Rotman
Attorney, Agent, or Firm—Cushman, Darby & Cushman

[57] ABSTRACT

The present invention deals with intermediate compounds, namely 4-(2'-, 3'- and 4'-pyridyl)-tetrahydropyrans and a process for their preparation. These compounds are prepared by reacting a 2'-haloethyl-3-(pyridyl)propyl ether with an alkali metal amide at −80° C. to 40° C.

7 Claims, No Drawings

PYRIDYL-TETRAHYDROPYRANS AND PROCESS FOR PREPARING SAME

This is a division of my copending application Ser. No. 804,933, filed Mar. 6, 1969, now U.S. Pat. No. 3,651,071.

This invention relates to pyridine derivatives and their manufacture and particularly to novel substituted pyridines and processes for the manufacture of substituted pyridines, and to a process for the manufacture of bipyridyls from substituted pyridines.

According to the present invention we provide a process for the manufacture of bipyridyls which comprises reacting the corresponding substituted pyridine with ammonia in the vapour phase, the substituted pyridine being a 2-(pyridyl)-tetrahydropyran or tetrahydrothiopyran, a 4-(pyridyl)-tetrahydropyran or -tetrahydrothiopyran or a substituted pyridine wherein the substituent is a group of the structural formula $-C(R)(R_1)(R_2)$ wherein R represents a hydrogen atom, a halogen atom, a hydroxy group, an alkoxy group or an amino group, and $R_1$ and $R_2$ each represents a group of the general formula $-CH_n(XR_3)_{2-n}\cdot CH_m(XR_4)_{3-m}$ wherein X represents an atom of oxygen or sulphur, $n$ is 0, 1 or 2 and $m$ is 1 or 2, and $R_3$ and $R_4$ each represents a hydrogen atom or an alkyl, alkene, aryl, alkaryl or cyclo-aliphatic group. In the pyridine derivatives (including the pyridyl tetrahydropyrans and tetrahydrothiopyrans), the substituent may be in the 2, 3 or 4 position in the pyridine nucleus.

The reaction is preferably carried out in the presence of molecular oxygen.

The substituted pyridine starting material in the vapour phase is heated with ammonia advantageously at a temperature in excess of 250° C, preferably 350°-450° C, for example about 380° C, usually in the presence of catalyst. Suitable catalysts include alumina, silica, silica-alumina, magnesia, chromia and mixtures thereof; these catalysts may contain platinum and/or palladium (as the metal or its oxide) in finely-divided form. Particularly suitable catalysts are the dehydrogenation catalysts, e.g. nickel, cobalt, copper, chromium and copper chromite. Preferably the reaction mixture contains molecular oxygen as, for example, oxygen gas which can be conveniently added in the form of air, although any molecular oxygen containing gas may be used.

The starting material can be vaporised simply by heating it to the required temperature and a particularly suitable technique is to drop the material in a stream of droplets onto a hot surface, for example onto a vaporiser or onto the catalyst for the reaction with ammonia. The material can be conveniently vaporised in a vaporiser prior to contact with the catalyst. Some of the starting materials are, however, tacky, viscous liquids or solids at ordinary temperatures and these are conveniently dissolved in a suitable solvent prior to vaporisation. Examples of suitable solvents for this purpose are water and alcohols, especially lower aliphatic alcohols and particularly methanol.

The bipyridyls produced by the process can be isolated from the reaction products by known techniques. For example, the gaseous reaction products can be condensed and the bipyridyl can then be isolated from the condensate by solvent extraction and/or fractional distillation, if desired under reduced pressure. If water is present in the reaction product obtained in the production of 4,4'-bipyridyls, these bipyridyls can be separated by filtration.

The process, whether a single or two-stage process, can be carried out batch-wise but has the advantage that it can be carried out as a continuous operation.

The process is particularly suitable for the production of 4,4'-bipyridyls although other isomers, for example 2,2'-, 2,4'-, 2,3'- and 3,4'-bipyridyls can be obtained by suitable choice of the starting material.

In addition to the compounds mentioned hereinbefore which can be reacted in the vapour phase with ammonia and oxygen to produce bipyridyls, there are a further class of substituted pyridines which can be converted to bipyridyls by the same reaction. These are substituted pyridines wherein the substituent contains a nitrogen atom and is a piperidyl group or a group of structural formula $-C(R)(R_9)(R_{10})$ wherein R is, and one of $R_9$ and $R_{10}$ may be, as hereinbefore defined but wherein at least one of the groups $R_9$ and $R_{10}$ has the general formula $-CH_2\cdot CH$, $-CH_2\cdot CON(R_5)(R_6)$ or $-CH_2\cdot CH_2N(R_7)(R_8)$ wherein $R_5$, $R_6$, $R_7$ and $R_8$ each represent a hydrogen atom or an alkyl, alkene, aryl, alkaryl, aralkyl or cyclic-aliphatic group. In this case, however, the presence of ammonia is not essential although it is beneficial.

According to the present invention therefore, we also provide a process for the manufacture of bipyridyls which comprises oxidising the corresponding substituted pyridine with molecular oxygen in the vapour phase, the substituted pyridine having a substituent which is a piperidyl group or a group of the formula $-C(R)(R_9)(R_{10})$ where R is as hereinbefore defined, $R_9$ represents a group of the general formula $-CH_2\cdot CN$, $-CH_2\cdot CON(R_5)(R_6)$ or $-CH_2\cdot CH_2N(R_7)(R_8)$ as defined in the immediately preceding paragraph, and $R_{10}$ represents a group as hereinbefore defined in respect of $R_1$ or $R_2$, but may in addition represent a group as defined in respect of $R_9$.

The reaction conditions for this process may be as described in respect of the reaction of substituted pyridines with ammonia, i.e. a temperature in excess of 250° C, preferably 350°-450° C in the presence of a catalyst. The reaction may be carried out batch-wise or as a continuous operation.

The starting materials for use in the processes of the invention are all substituted pyridine derivatives and the majority of them are novel compounds. Moreover, the substituted pyridines wherein the substituent has the general formula $-C(R)(R_1)(R_2)$ or $-C(R)(R_9)(R_{10})$ may be derived from substituted pyridines wherein the substituent has the formula $-CH(R)(R_1)$ or $-CH(R)(R_9)$ respectively and the majority of these substituted pyridines are also novel compounds.

According to a further feature of the present invention, therefore, we provide, as novel compounds, 4-(pyridyl)-tetrahydropyrans or tetrahydrothiopyrans and 2-(pyridyl)-tetrahydropyrans or tetrahydrothiopyrans. The tetrahydropyranyl or tetrahydrothiopyranyl group may be attached to the carbon atom in the 2, 3 or 4 position in the pyridyl nucleus.

According to a still further feature of the present invention we provide, as novel compounds, substituted pyridines wherein the substituent has the structural formula $-C(R)(R_1)(R_2)$ or $-C(R)(R_9)(R_{10})$ wherein the groups R, $R_1$, $R_2$, $R_9$ and $R_{10}$ are as hereinbefore defined and wherein $R_2$ and $R_{10}$ may in addition be a hydrogen atom but wherein both of $R_1$ and $R_2$ are not the group $-CH_2\cdot CH_2OH$ and both of $R_9$ and $R_{10}$ are not the group $-CH_2\cdot CONH_2$.

We also provide the novel compounds pyridyl 1-alkylpiperidines wherein the alkyl group contains at least 2 carbon atoms.

Unsubstituted 4-(pyridyl)tetrahydropyrans have the following structural formula:

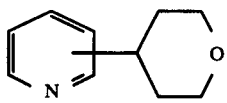

and included within the present invention are compounds having this basic formula but containing one or more substituents, for example alkyl or alkoxy groups in either or both of the pyridyl or tetrahydropyranyl nuclei.

Unsubstituted 2-(pyridyl)tetrahydropyrans have the structural formula:

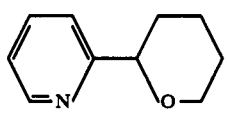

and other compounds within the scope of the invention are those wherein either or both of the heterocyclic nuclei are substituted, for example by alkyl or alkoxy groups, especially compounds of formula

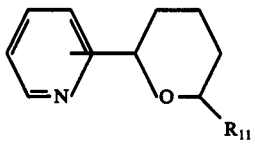

wherein $R_{11}$ represents an alkyl group, an alkoxy group, a heterocyclic group containing a N-heteroatom (which is linked to the carbon atom of the tetrahydropyranyl group) which may also contain one or more other heteroatoms for example a

group, or a dialkylamine group for example a —$N(CH_3)_2$ group.

The other novel substituted pyridines of the invention have the basic structural formula

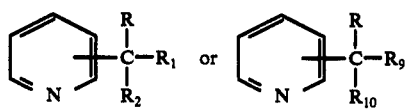

and included within the scope of the invention are compounds having this basic formula but which contain one or more substituents, for example alkyl groups on one or more of the other carbon atoms of the pyridine nucleus. Also included are compounds of the above basic formula but having a substituent on the nitrogen atom, for example substituted pyridine N-oxides.

4-(pyridyl)-tetrahydropyrans, -tetrahydrothiopyrans, or -piperidines can be made by reacting a 2'-haloethyl-3-(pyridyl)-propylether, thioether or amine respectively with an active alkali metal comound. The reagents are preferably reacted in equimolar proportions and preferably at a temperature in the range $-10°$ C to $-80°$ C in solution in a medium containing liquid ammonia. However, the reaction may be carried out in the absence of a solvent or in solvents other than liquid ammonia, for example hydrocarbons and ethers, in which case higher temperatures, e.g. up to 40° C, may be employed. Higher temperatures can also be achieved by carrying out the reaction under superatmospheric pressure. The preferred active alkali metal compounds are alkali metal amides, especially sodamide.

The 4-(pyridyl)-tetrahydropyran, -tetrahydrothiopyran, or -piperidine may be isolated from the reaction mixture by conventional techniques, for example by decomposing any excess metal amide by addition of an ammonium salt; extraction of the resultingproduct with an organic solvent which is liquid at ordinary temperatures e.g. ether; washing the organic layer with water and separating the organic solvent and the product by distillation.

The 2'-haloethyl 3-(pyridyl)propyl ethers, thioethers and amines are novel compounds. In their unsubstituted forms these compounds have the general structural formula

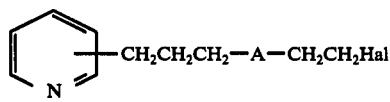

where A is O, S, or $NR_{12}$ wherein $R_{12}$ may be any inert substituent for example hydrogen or an alkyl group, and Hal respresents a halogen atom.

2'-haloethyl 3-(pyridyl)propyl ethers, thioethers or amines can be produced by interacting an alkali metal derivative of a picoline with a di-(2-haloethyl)ether, thioether, or amine.

The alkali metal derivative of the picoline may be made by interaction of the picoline with an active alkali metal compound e.g. an alkali metal amide (produced for example by dissolving an alkali metal in liquid ammonia in the presence of ferric ions) or an alkyl derivative of an alkali metal e.g. a lithium alkyl. The preferred method of making the alkali metal derivative of the picoline comprises interaction of equimolar proportions of sodamide or potassamide with the picoline which, if the 4-pyridyl derivative is required is a 4-(or gamma)-picoline, at a temperature in the range $-40°$ C to $-80°$ C in solution in a medium containing liquid ammonia. The reaction may be carried out under pressure to enable temperatures above $-30°$ C to be employed.

The alkali metal derivative of the picoline may be reacted with the di-(2-haloethyl)ether, thioether or amine by addition of the former to the latter and ensuring a stoichiometric excess of the latter throughout the reaction. The addition may conveniently be carried out at a temperature of from $-10°$ C to $-80°$ C preferably using equimolar proportions of the reagents. However, temperatures of up to 40° C may be employed, if necessary by carrying out the reaction under increased pressure. The reaction may conveniently be carried out in solution, for example in a solvent comprising or containing liquid ammonia.

The di-(2-haloethyl)ether, thioether or amine is preferably a di-(2-chloroethyl)ether, thioether or amine.

2-(pyridyl)-tetrahydropyrans or tetrahydrothiopyrans can be prepared by the reaction of the appropriate pyridyl lithium or pyridyl Grignard reagent with a 2-halotetrahydropyran or tetrahydrothiopyran. The pyridyl group becomes attached to the tetrahydropyranyl group by the carbon atom which carried the lithium atom or the Grignard reagent radical. 2-pyridyl lithium can be prepared by reacting 2-chloro-, or preferably 2-bromopyridine with n-butyl lithium at low temperatures, for example below 0° C and preferably about −40° C or lower. 4-pyridyl lithium can similarly be prepared from 4-bromo- or 4-chloro-pyridine. 2-pyridyl Grignard reagents are easily prepared by reacting 2-bromo-pyridine with e.g. magnesium in the presence of an alkyl halide, e.g. an alkyl bromide by the 'entrainment' procedure of Overhoff and Proost (Rec. Trav. Chim. 57, 179, (1938). 4-pyridyl Grignard reagents can similarly be prepared from 4-bromopyridine. In each case the reagents need simply be mixed but if desired an inert organic solvent may be employed. Any inert solvent may be used, for example aliphatic or aromatic hydrocarbons, ethers and ketones, but in view of the low temperatures employed the solvent preferably has a freezing point of below −50° C.

The pyridyl and/or the tetrahydropyranyl or tetrahydrothiopyranyl nuclei may be substituted and examples of substituents which may be present are halogen atoms, alkyl groups and alkoxy groups, and the tetrahydropyran or tetrahydrothiopyran may also carry a heterocyclic substituent. In particular, the tetrahydropyran may have the formula

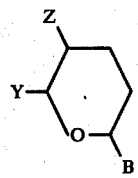

where Y represents a chlorine atom or a bromine atom, Z represents a halogen atom or a hydrogen atom, and B represents a hydrogen atom, an alkyl or alkoxy group (especially a methoxy group), a heterocyclic group e.g. of formula

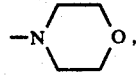

or an amine group e.g. —N(CH$_3$)$_2$. The stereochemistry of the tetrahydropyranyl is not important.

The reaction between the pyridyl lithium or pyridyl Grignard reagent and the 2-halo-tetrahydropyran or tetrahydrothiopyran can be effected simply by mixing the reagents but if desired either or both of the reagents may be employed in the form of a solution. It is an advantage that the reagents do not require to be separated from the reaction mixture in which they have been prepared and thus if they are prepared in solution it is sufficient simply to mix the resulting solutions. The temperature will usually be maintained below 0° C and preferably about −40° C or below since the reagents tend to be unstable at ordinary temperatures.

The 2-pyridyl tetrahydropyrans or tetrahydrothiopyrans wherein B of the tetrahydrothiopyranyl residue (see above) is a hydrogen atom can be separated from the reaction mixture in which they have been prepared by allowing the mixture to warm to room temperature, acidifying it for example by adding hydrochloric acid, and separating the resulting organic and aqueous phases. The organic phase is then neutralised and extracted with ether, and the extract fractionally distilled to recover the fairly pure product which can be purified by further fractional distillation.

The product wherein B of the tetrahydrothiopyranyl residue (see above) is other than a hydrogen atom can be separated by adding an ammonium salt of an acid and then separating the resulting phases, extracting with ether and distilling as above. The ammonium salt, for example ammonium chloride, is preferably used in the form of a solution which advantageously can be an aqueous solution.

Substituted pyridines wherein the substituent has the structural formula —C(R)(R$_1$)(R$_2$) or —C(R)(R$_9$)(R$_{10}$) can be prepared by reacting the appropriate pyridine derivative with a metal amide or an organo-lithium compound and with an appropriate halogenated organic compound or (if a group —CH$_2$.CH$_2$OH, —CH$_2$.CH$_2$SH or CH$_2$CH$_2$NH$_2$ is to be introduced) with an alkylene-oxide, -sulphide or -imine. Particular combinations of pyridine derivatives and chlorinated organic compounds or alkylene compounds are discussed in more detail hereinafter.

Pyridyl alkane diols, pyridyl alkane dithiols or pyridyl alkane diamines can be prepared by reacting an alkyl pyridine with a metal amide or an organolithiums compound and with an alkylene oxide, alkylene sulphide or alkylene imine respectively. This process is especially suitable for the production of 3-(4'-pyridyl)-pentane-1,5-diol; 3-(4'-pyridyl)-pentane-1,5-dithiol or 3-(4'-pyridyl)-pentane-1,5-diamine by reacting gamma-picoline with a metal amide or an organolithium compound and with ethylene oxide, ethylene sulphide or ethylene imine respectively.

The reaction can if desired be carried out simply by mixing the reagents in appropriate amounts in the absence of a solvent, but usually it is carried out in a solvent for the pyridine derivative. Any solvent may be employed which is inert to the reactants and to the reaction product. Alternatively an excess of the alkyl pyridine or alkanolpyridine or of pyridine itself may be provided to act as a solvent. A particularly suitable solvent for use in reactions involving a metal amide is liquid ammonia although others, for example organic amines such as diethylamine may be used. Examples of solvents which may be used when an organolithium compound is employed are hydrocarbons, especially aliphatic ethers, and particularly diethyl ether, and dimethyl sulphoxide, especially a solution of the sodium salt of dimethyl sulphoxide in excess dimethyl sulphoxide.

The temperature at which the reaction is carried out is to some extent dependent upon the particular solvent employed and the pressure at which the reaction is effected. Thus when liquid ammonia is employed as the solvent at ordinary pressure, the temperature should be −33° C or below but temperatures above this, for example up to room temperature may be employed using an amine or an ether as the solvent. Usually, however, the reaction is carried out at a temperature below 40° C.

Temperatures higher than those mentioned above may be used, and these can be achieved by carrying out the reaction under superatmospheric pressure, for example in an autoclave.

The metal amide may be in particular an alkali metal amide, particularly sodamide or potassamide. The amide may be added as the pre-formed compound or it may be formed in situ. For example sodamide or potassamide can be formed in situ by adding metallic sodium or potassium to anhydrous liquid ammonia in the presence of a catalyst, for example ferric nitrate (ferric ions). The organolithium compound may be in particular a lithium alkyl, for example lithium ethyl or lithium butyl, or a lithium phenyl or lithium benzyl.

As stated hereinbefore the new compounds of the invention can be prepared from a pyridine derivative and the appropriate halogenated organic compound. Pyridine derivatives which may be used include those of formula

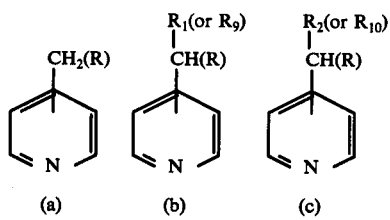

wherein $R$, $R_1$, $R_2$, $R_9$ and $R_{10}$ are as hereinbefore defined.

The halogenated organic compounds which can be reacted with the pyridine derivative have the formula D Hal wherein D represents $R_1$, $R_2$, $R_9$, or $R_{10}$ as hereinbefore defined and Hal is a halogen atom, especially a chlorine atom. The product obtained by reacting pyridine derivative (a) with halogenated organic compound D Hal can have the formula

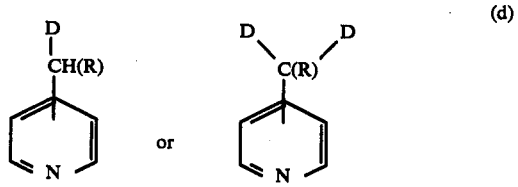

depending upon whether 1 mole or 2 moles of D Hal are employed per mole of the pyridine derivative.

The pyridine derivatives (b) and (c) (prepared for example as described in the immediately preceding paragraph) can be reacted with the organic compound D Hal to form the compound (d). Alternatively the compounds (d) can be prepared by reacting pyridine derivatives (b) with a metal amide or an organolithium compound and an alkylene oxide, alkylene sulphide or alkylene imine, particularly an ethylene conpound. The use of alkylene compounds having 3 or more carbon atoms has the advantage that the aliphatic group introduced into the pyridine nucleus may have an alkyl group as substituent; bipyridyls wherein the pyridine nuclei carry alkyl substituents can be obtained from these derivatives.

A particular pyridine derivative which can be used is 1-(4'-pyridyl)-n-propane-ol or -thiol which can be produced by reacting gamma picoline with a metal amide and with ethylene oxide or ethylene sulphide in amounts such that the mole ratio of metal amide:gamma picoline is about 1:1 and of ethylene compound: gamma picoline is also about 1:1.

The products can be separated from the reaction mixture in which they are formed in any convenient manner. For example, especially if the compound has been prepared in liquid ammonia, ammonium chloride can be added and the ammonia (or other solvent) removed by evaporation. The amount of ammonium chloride is usually at least 1 mole per mole of product to be separated. The residue is extracted with a solvent, for example pyridine, methylene chloride or diethyl ether which is then allowed to evaporate. The reaction product is then isolated from the residue by fractional distillation under reduced pressure. In the case where pyridyl alkane diols, dithiols or diamines are prepared from gamma picoline and an alkylene oxide, sulphide or imine respectively, the amounts of the metal amide or organolithium compound and of the alkylene derivative used are preferably at least 2 moles of the alkylene derivative and at least 2 moles of the metal amide or organolithium compound per mole of the alkylpyridine. It is especially preferred that the amounts of both the alkylene derivative and the metal amide or organolithium compound are slightly above 2 moles per mole of the alkyl pyridine. The metal amide or the organolithium compound can be added before the alkylene derivative or the three reagents can be mixed together initially.

Pyridyl tetrahydropyrans or tetrahydrothiopyrans can also be prepared by heating the appropriate pyridyl alkane diol or dithiol at a temperature of at least 250° C, preferably in the presence of a catalyst. Pyridyl piperidines can be prepared by heating the appropriate pyridyl alkane diol, dithiol or hydroxyl thiol in the presence of ammonia; in this case the temperature should be below that at which dehydrogenation of the piperidyl group can occur. Pyridyl tetrahydrothiopyrans can also be prepared by heating the appropriate pyridyl alkane diol in the presence of hydrogen sulphide, or by heating a pyridyl alkane (hydroxyl thiol) in the presence or absence of hydrogen sulphide.

The simplest pyridyl alkane diol and dithiol which may be used are 3-(pyridyl)-pentane-1,5-diol or dithiol. The diol or dithiol may be employed without isolation from the mixture in which it has been prepared. The temperature at which the diol or dithiol is heated to convert it to the corresponding pyridyl cyclic ether, pyridyl cyclic thioether or pyridyl piperidine (if ammonia is present) is at least 250° C, and preferably is at least 300° C. We especially prefer to employ a temperature of the order of 380° C. It is sufficient simply to heat the diol or dithiol at the desired temperature, but we prefer to carry out the heating in the presence of a dehydration catalyst, for example alumina, silica, silica/alumina or mixtures thereof. A particularly convenient technique is to pass the diol or dithiol in vapour phase through a bed of the catalyst contained in a tube, for example a glass tube. If desired the heating may be carried out under super-atmospheric pressure, in which case lower temperatures may be needed to effect the conversion. Ammonia or hydrogen sulphide may be added to or dissolved in the diol or dithiol so that the product of heating the diol or dithiol is the corresponding pyridyl piperidine or pyridyl alkane dithiol respectively.

The invention is illustrated but in no way limited by the following Examples:

EXAMPLE 1

To stirred liquid ammonia (3 liters) was added ferric nitrate (0.1 gm) followed by sodium metal (24 gms in 1 gm pieces over a period of 40 minutes). To the resulting solution gamma-picoline (46.6 gms) was added over a period of 3 minutes and a deep yellow colour was allowed to develop over a period of 2 hours. Liquid ethylene oxide (44.0 gms) was added and the mixture was stirred for a further 8 hours. Solid ammonium chloride (55 gms) was added in small quantities and the solvent was allowed to evaporate overnight. The tacky residue was extracted into pyridine and the pyridine was then evaporated. The residual oil was dissolved in an equal quantity of hot water and dropped onto a bed of alumina (Actal 'A') heated at 380° C at the rate of 1 ml/minute using a 300 ml/minute flow of nitrogen as carrier gas. The effluent was condensed and the condensate extracted into carbon tetrachloride. Evaporation of the solvent followed by distillation yielded 4-(4-pyridyl)-tetrahydropyran (19 gms - 42% conversion based on gamma-picoline fed).

EXAMPLE 2

To stirred liquid ammonia (300 mls) was added ferric nitrate (50 mgms) and sodium metal (1.2 gms). The mixture was allowed to stand for 30 minutes and then gamma-picoline (4.7 gms) was added. A deep yellow colour was allowed to develop over a period of 2 hours. Cooled ethylene oxide (2.2 gms) was then added and the mixture was stirred for a further 4 hours, yielding a solution designated "Solution A".

To stirred liquid ammonia (200 mls) was added ferric nitrate (50 mgms) and sodium metal (1.2 gms). The mixture was allowed to stand for 30 minutes and was then added over a period of 2 minutes to Solution A. The mixture was stirred for a further 4 hours after which time solid ammonium chloride (6 gms) was added slowly. The solvent was allowed to evaporate overnight and the residue was extracted into methanol (100 mls) and filtered.

The filtrate was vaporised at 25 mls/hr and fed in a stream of nitrogen carrier gas (100 mls/minute) over a 4 inch bed of 13% silica-alumina in a 1 inch glass tube at a temperature of 340° C. The liquid reactor effluent was analysed by gas/liquid chromatography and was found to contain 4-(4-pyridyl)-tetrahydropyran (62% conversion).

EXAMPLE 3

To stirred liquid ammonia (300 mls) was added ferric nitrate (50 mgms) and potassium metal (2.0 gms). The mixture was allowed to stand for 30 minutes after which time gamma-picoline (4.7 gms) was added. A deep yellow colour was allowed to develop over a period of 2 hours. Cooled ethylene oxide (2.2 gms) was then added and the mixture was stirred for a further 4 hours, yielding a solution designated "Solution B".

To stirred liquid ammonia (200 mls) was added ferric nitrate (50 mgms) and potassium metal (2.0 gms). The mixture was allowed to stand for 30 minutes and added over a period of 2 minutes to Solution B. The mixture was stirred for a further 4 hours after which time solid ammonium chloride (6 gms) was slowly added. The solvent was allowed to evaporate overnight and the residue was extracted into methanol (100 mls) and filtered.

The filtrate was vaporised at 25 mls/hour and fed in a stream of nitrogen carrier gas (100 mls/minute) over a 4 inch bed of 13% silica-alumina in a 1 inch bore glass reactor tube at a temperature of 340° C. The liquid reactor effluent was analysed by gas/liquid chromatography and was found to contain 4-(4-pyridyl)-tetrahydropyran (58% conversion based on gamma-picoline fed).

EXAMPLE 4

To stirred liquid ammonia (2 liters) was added ferric nitrate (0.1 gm) followed by sodium metal (18.5 gms) in 1 gram pieces over a period of 30 minutes. The mixture was allowed to stand for 30 minutes and then gamma-picoline (37.3 gms) was added to it. A deep yellow colour was allowed to develop over 2 hours, after which time ethylene sulphide (48.0 gms) was added as quickly as possible. The resulting solution was stirred for a further 4 hours after which ammonium chloride (50 gms) was slowly added, followed by diethyl ether (1 liter). The ammonia was allowed to evaporate and the residual solution was filtered. The solvent was evaporated from the filtrate and the residue was distilled to yield 3-(4-pyridyl)-pentane-1,5-dithiol (18 gms) as a yellow oil of b.p. 163°-165° C. The product had the following spectra:

I.R. $\nu$max ($CCl_4$) 3100, 3050, 2950, 2850, 2500, 1600, 1440, 1430, 1410, 1270 and 1075 cm$^{-1}$ NMR $\tau$($CCl_4$) 1.45, 2.8, 7 - 8.5 (Relative Intensities 2:2:11)

M.S. M/$\epsilon$ = 213.0658 ($C_{10}H_{15}NS_2$ has M/$\epsilon$ = 213.0646), 179

A low-boiling by-product of the reaction was identified as 3-(4-pyridyl)-propane-1-thiol (b.p. 84° - 86° C/1 mm. Hg) identified by the following spectra:

I.R. $\nu$ max (liquid film) 3100, 3050, 2950, 2850, 2550, 1600, 1430, 995 and 810 cm$^{-1}$ M.S. M/$\epsilon$ = 153.0613 ($C_8H_{11}NS$ has M/$\epsilon$ = 153.0612)

EXAMPLE 5

Ferric nitrate (0.1 gm) was added to stirred liquid ammonia (3 liters) at −30° C. Sodium metal (24 gms) was added to the stirred mixture over a period of 45 minutes and then gamma-picoline (46.6 gms) was added to the resulting solution over a period of 3 minutes. The solution was stirred for 2 hours during which time it developed a yellow colouration.

After this time liquid ethylene oxide (44.0 gms) was added and the mixture was then stirred for 8 hours. Solid ammonium chloride (55 gms) was then added in small quantities after which the mixture was allowed to stand overnight to allow the ammonia to evaporate. The resulting tacky residue was extracted into pyridine which was then removed by evaporation, leaving a liquid which on distillation yielded 3-(4-pyridyl)-pentane-1,5-diol (66 gms), representing a conversion of 73% based on the gamma-picoline fed. The product at this stage had a boiling range of 182° to 190° C at 0.5 mm Hg pressure, and a melting range of 66° to 68° C. After recrystallisation from water the product had a melting point of 72° to 73° C.

The 3-(4-pyridyl)-pentane-1,5-diol was identified by the following infra-red (IR), nuclear magnetic resonance (NMR) and mass (MS) spectra:

IR (melt) 3500, 2950, 2850, 1600, 1420, 1050, 1005 cm$^{-1}$

NMR $\tau$($CD_3OD$) 1.52, 2.65, 5.05, 6.6, 6.95, 8.1 (Relative Intensities 2:2:2:4:1:4)

MS M/$\epsilon$ = 181.1103 ($C_{10}H_{15}NO_2$ has M/$\epsilon$ = 181.1102)

EXAMPLE 6

To stirred liquid ammonia (3 liters) was added ferric nitrate (0.1 gm) followed by sodium metal (24 gms) in 1 gram pieces over a period of 30 minutes. The resulting solution was stirred for 30 minutes after the final addition of sodium metal and then a solution of gamma-picoline (46.6 gms) and ethylene oxide (48 gms) in ice-cold diethyl ether (100 mls) was added over a period of 2 hours. The mixture was stirred for a further 2 hours and then solid ammonium chloride (55 gms) was added. The solvent was allowed to evaporate overnight and the residual tacky solid was extracted into pyridine. Evaporation of the pyridine followed by fractional distillation yielded 3-(4-pyridyl)-pentane-1,5-diol of boiling range 200° to 202° C at 1 mm Hg pressure and melting range 66° to 68° C (56 gms 62% conversion of gamma-picoline fed).

EXAMPLE 7

Sodamide (25 gms), gamma-picoline (24 gms) and ethylene oxide (24 gms) were introduced into a pressure vessel cooled to 0° C. The vessel was sealed and heated to +20° C and was then maintained at +20° C with vigorous stirring for 6 hours. After this time the pressure was then released and methanol (50 mls) was introduced slowly, followed by dilute hydrochloric acid (200 mls). The solution was evaporated to dryness, neutralised with aqueous potassium carbonate solution and again evaporated to dryness. The residual tacky solid was extracted into pyridine, the solvent was evaporated and the residual oil was distilled to yield 3-(4-pyridyl)-pentane-1,5-diol (8 gms, 18%).

EXAMPLE 8

S odamide (25 gms), gamma-picoline (24 gms) and ethylene oxide (24 gms) were introduced into a pressure vessel cooled to −1 40° C. Liquid ammonia (70 mls) was introduced and the vessel was then sealed. The mixture was heated to +20° C and maintained at that temperature, with vigorous stirring, for 2 hours. The ammonia was then vented off. Methanol (50 mls) was introduced slowly, followed by dilute hydrochloric acid (200 mls). The solution was evaporated to dryness, neutralised with aqueous potassium carbonate solution and again evaporated to dryness. The residual tacky solid was extracted into pyridine, the solvent was evaporated and the residual oil was distilled to yield 3-(4-pyridyl)-pentane-1,5-diol (28 gms, 62%).

EXAMPLE 9

To stirred liquid ammonia (3 liters) was added ferric nitrate (0.1 gm) followed by sodium metal (24 gms) in 1gram pieces over a period of 30 minutes. The mixture was allowed to stand for 30 minutes and ethylene oxide (45 gms) was added, followed by alpha-picoline (45.6 gms). The resulting blood-red solution was stirred for 4 hours and then ammonium chloride (60 gms) was added in small portions. The solvent was allowed to evaporate overnight and the residual oily residue was extracted into pyridine. Evaporation of the solvent and distillation of the residual oil yielded 3-(2-pyridyl)-pentane-1,5-diol (42 gms, 46% conversion), M.P. 44° C b.p. 176° to 180° C at 1 mm Hg.

The product had the following spectra:
IR (liquid film) 3400, 2950, 1595, 1470, 1430, 1050, 1000 and 755 cm$^{-1}$
NMR $\tau$ [(CD$_3$)$_2$CO] 1.52, 2.38, 282, 5.7, 6.6, 6.85 and 8.1 (Relative Intensities 1:1:2:2:4:1:4)
MS M/$\epsilon$ = 182, 181.1089 (C$_{10}$H$_{15}$NO$_2$ has M/$\epsilon$ = 181.1102) 180, 137, 120, 118, 117, 106.

EXAMPLE 10

To stirred liquid ammonia (3 liters) was added ferric nitrate (0.1 gm) followed by potassium metal (40 gms) in 1 gram pieces over a period of 30 minutes. The mixture was allowed to stand for 30 minutes and ethylene oxide (45 gms) was added followed by beta-picoline (45.6 gms). The resulting dark-red solution was stirred for 24 hours and ammonium chloride (60 gms) was added in small portions. The solvent was allowed to evaporate overnight and the residual oily residue was extracted into pyridine. Evaporation of the pyridine and distillation of the residual oil yielded 3-(3-pyridyl)-pentane-1,5-diol (18 gms, 20% conversion), b.p. 200° to 210° C at 1 mm Hg.

The product had the following spectra:
I.R. (liquid film) 3400, 2950, 2900, 1600, 1460, 1430, 1050, 880, 820 and 720 cm$^{-1}$
M.S. M/$\epsilon$ = 181.1088 (C$_{10}$H$_{15}$NO$_2$ has M/$\epsilon$ = 181.1102)

EXAMPLE 11

3-(4-pyridyl)-pentane-1,5-diol (5 gms) was distilled at atmospheric pressure. The distillate was extracted into ether and the solution was washed with water and dried over magnesium sulphate. Evaporation of the solvent and distillation of the residual oil yielded 4-(4-pyridyl)-tetrahydropyran (2.2 gms - 58% conversion of diol fed).

EXAMPLE 12

A solution of n-butyl bromide (46 g) in dry ether (100 mls) was added slowly to a suspension of lithium wire (2.3 g) in dry ether (200 mls), at a temperature of −20° C with vigorous stirring under an atmosphere of nitrogen. Stirring was continued after the addition was completed for 2½ hours at −20° C. The reaction mixture was then filtered under nitrogen and cooled to between −45° C and −40° C, and 2-bromopyridine (52.7 g) in dry ether (10 mls) was added slowly to the filtrate, the temperature being maintained at −40° C. A dry nitrogen atmosphere was maintained, and after the addition was completed, stirring was continued at −40° C for 2 hours (Solution A).

Δ$^2$-dihydropyran (28 g) in dry ether (100 mls) was cooled to −10° C and dry hydrogen chloride gas (12.2 g) was passed into it at such a rate that the temperature did not rise above −10° C. The solution was cooled to −40° C and added slowly, with stirring, under nitrogen to Solution A also cooled to −40° C. Stirring was continued for 1 hour at −40° C, and the reaction product was then allowed to warm to room temperature. Hydrochloric acid (200 mls of 2N HCl) was added and the mixture was separated. The acidic fraction was neutralised with sodium carbonate solution and extracted with ether. The extracts were washed, dried and fractionally distilled to yield:
a. 2-bromo pyridine - b.p. 66° to 80° C/3.5-5mm Hg (25 g, 48%).
b. Product (14 g, 26% conversion, 52% yield).

The product had a boiling range of 70° to 73° C/1 mm Hg.

The product was identified as 2-(2'-pyridyl)-tetrahydro pyran by the following infra-red, mass (MS) and nuclear magnetic resonance (NMR) spectra:
Infra-red:$\nu$ max (liquid film) 2940, 2840, 1600, 1460, 1430, 1200, 1070, 1040, 1110, 910 and 765 cm$^{-1}$
N.M.R. $\tau$(CCl$_4$) 1.55, 2.5, 2.95, 5.65, 5.9, 6.45, 8.5 (Relative intensities 1:2:1:1:1:1:6)

M.S. M/ε = 163.0997 ($C_{10}H_{13}NO$ has M/ε = 163.0997), 106, 93, 85, 79.

Using alpha-picoline instead of gamma-picoline in the preparation of Solution A, and continuing the reaction under the conditions outlined above yielded 1-(2-chloroethoxy)-3-(2-pyridyl)-propane (25 gms) b.p. 105° to 115° C/15 mm Hg, characterised by the following spectral data:

I.R. (liquid film) 2950, 2850, 1580, 1470, 1430, 1120, 770 and 750 cm$^{-1}$

N.M.R. τ($CCl_4$) 1.5, 2.5, 2.95, 6.43, 6.54, 7.15, 8.0 (Relative intensities 1:1:2:4:2:2:2)

M.S. M/ε = 199, 198.0680 ($C_{10}H_{13}NOCl$ has M/ε = 198.0685, loss of H), 164

Using beta-picoline instead of gamma-picoline in the preparation of Solution A, and continuing the reaction under the conditions outlined above yielded 1-(2-chloroethoxy)-3-(3-pyridyl)-propane (8 gms — as an unstable straw-coloured liquid).

M.S. M/ε = 199

EXAMPLE 13

To stirred liquid ammonia (1 liter) was added ferric nitrate (0.1 gram) followed by potassium metal (20.0 grams) in 1 gram pieces over a period of 30 minutes. To the resulting solution gamma-picoline (46.6 grams) was added over a period of 3 minutes and a deep yellow colour was allowed to develop.

The solution was added to a stirred solution of 2,2'-di(chloroethyl)-ether (72.0 grams) in liquid ammonia (1 liter) at such a rate (total addition taking 20 minutes) that no yellow colour persisted, yielding a solution designated Solution A.

To stirred liquid ammonia (1 liter) was added ferric nitrate (0.1 gram) followed by potassium metal (20.0 grams) in 1 gram pieces over a period of 30 minutes. The resulting solution was stirred for 20 minutes and added to Solution A at such a rate that only a pale yellow colour developed. The mixture was stirred for 1 hour and ammonium chloride (20 grams) was added slowly by ether (1 liter). The mixture was allowed to warm to room temperature, was filtered, and washed with water. The solvent was removed and the residue was distilled to give 4-(4-pyridyl) tetrahydropyran (30 grams) having the following properties:

Boiling point 115°-118° C/1 mm Hg

Melting point 60°-62° C

Infra-red ν max (liquid film) 3070, 3025, 2940, 2845, 1600, 1410, 1130, 1085, 990 and 900 cm$^{-1}$ NMRτ($CDCl_3$) 1.5, 2.85, 5.9, 6.5, 7.25, 8.25 (Relative intensities 2:2:2:2:1:4)

Mass spectra: M/ε = 163.0998 ($C_{10}H_{13}NO$ has M/ε = 163.0997) 132, 130, 119, 105, 92 and 78

A higher boiling fraction (5 gms) was also collected and identified as di-3-(4-pyridyl)-prop-1-yl ether b.p. 215° C/1 mm Hg.

Infra red ν max ($CCl_4$) 3070, 3025, 2940, 2845, 1600, 1410, 1120, 990 and 900 cm$^{-1}$ NMR τ[($CD_3$)$_2$CO]: 1.35, 2.7, 6.5, 7.2, 8.1 (Relative intensities 4:4:4:4:4)

M.S. M/ε = 256.1578 ($C_{16}H_{20}N_2O$ has M/ε = 256.1576)

Similarly from alpha-picoline was obtained 4-(2-pyridyl) tetrahydropyran identified by the following spectral data:

M.S. M/ε 163 ($C_{10}H_{13}NO$ has M/ε 163)

Also obtained from this reaction was vinyl 3-(2-pyridyl)-prop-1-yl ether b.p. 85° C/0.5 mm Hg identified by the following spectral data:

I.R. (liquid film) 3050, 2950, 2850, 1640, 1620, 1580, 1560, 1460, 1430, 1300, 1195, 990, 820, 770 and 750 cm$^{-1}$ N.M.R. τ($CCl_4$) 1.55, 2.5, 3.0, 3.6, 5.95, 6.15, 6.4, 7.2 and 7.95 (Relative intensities 1:1:2:1:1:1:2:2:2)

M.S. M/ε = 163.0985 ($C_{10}H_{13}NO$ has M/ε = 163.0997).

Similarly from beta-picoline was obtained 4-(3-pyridyl) tetrahydropyran, m.p. 340° C identified by the following spectral data:

I.R. ν max ($CCl_4$) 2950, 2850, 1460, 1440, 1430, 1375, 1120, 1090, 1020 and 900 cm$^{-1}$ N.M.R. τ($CCl_4$) 1.5, 2.5, 2.8, 5.95, 6.5, 7.2 and 8.25 (Relative intensities 2:1:1:2:2:1:4)

M.S. M/ε = 163.1004 ($C_{10}H_{13}NO$ has M/ε = 163.0997)

EXAMPLE 14

Solution A prepared as in Example 13 was stirred for 1 hour and ammonium chloride (20 gms) was added slowly followed by ether (1 liter). The mixture was allowed to warm to room temperature, was filtered and washed with water. The solvent was removed by distillation under vacuo and the residue was heated at 80° C/1 mm Hg to remove starting materials. The residue was purified by column chromatography to give 1-(2-chloroethoxy)-3-(4-pyridyl) propane (60 grams) an amber-coloured liquid, which could not be distilled without decomposition and which had the following properties:

Infra-red ν max (liquid film) 3075, 3020, 2950, 2860, 1600, 1415, 1300, 1120, 990, 800 and 660 cm$^{-1}$ NMRτ($CCl_4$) 1.5, 2.85, 6.3, 6.55, 7.3, 8.15 (Relative intensities 2:2:4:2:2:2)

M.S. M/ε = 199.0751 ($C_{10}H_{14}NClO$ has M/ε = 199.0763)

EXAMPLE 15

To stirred liquid ammonia (1 liter) was added ferric nitrate (0.1 gm) followed by potassium metal (4.5 gms) in 1 gram pieces over a period of 5 minutes. The resulting solution was allowed to stand for 30 minutes and was then added with stirring to a solution of 2-chloroethyldimethylamine hydrochloride (14.4 gms) in liquid ammonia (1 liter). The resulting solution was designated "Solution A".

To stirred liquid ammonia (1 litre) was added ferric nitrate (0.1 gm) followed by potassium metal (4.5 gms) in 1 gram pieces over a period of 5 minutes. The mixture was allowed to stand for 20 minutes and 3-(4-pyridyl)-propionaldehyde diethyl acetal (21 gms) was then added over a period of 2 minutes. A yellow colour was allowed to develop over a period of 2 hours, and after this time the solution was added to Solution A.

The resulting mixture was stirred for 3 hours after which time solid ammonium chloride (8 gms) was added followed by diethyl ether (500 mls). The ammonia was allowed to evaporate overnight and the residual mixture was then filtered. The solvent was evaporated from the filtrate and the residual oil was distilled to yield 3-(4-pyridyl)-1,1-diethoxy-5-dimethylamino pentane (18 gms, 72% conversion of starting material fed); b.p. 140° C/1 mm Hg pressure.

The product was identified by the following infra red (IR), nuclear magnetic resonance (NMR) and mass (MS) spectra: I.R. (liquid film) 2950, 2850, 2780, 1600, 1120, 1069, 1000 and 820 cm$^{-1}$ N.M.R. $\tau$(CCl$_4$) 1.5, 2.9, 5.8, 6.55, 7.15, 7.9, 8.05, 8.85 (Relative intensities 2:2:1:4:1:8:4:6)

M.S. M/$\epsilon$ 280, 251.1759 (C$_{14}$H$_{23}$N$_2$O$_2$ has M/$\epsilon$ 251.1752, loss of C$_2$H$_5$).

EXAMPLE 16

To stirred liquid ammonia (2 liters) was added ferric nitrate (0.1 gm) followed by potassium metal (12 gms) in 1 gram pieces over a period of 20 minutes. To the resulting solution was added 3-(4-pyridyl)-1-dimethylamino pentane (49 gms) over a period of 3 minutes and a deep yellow colour was allowed to develop over a period of 2 hours. Liquid ethylene oxide (22 gms) was added and the mixture was stirred for a further 3 hours. Solid ammonium chloride (20 gms) was then added in small portions followed by diethyl ether (1 liter). The ammonia was allowed to evaporate overnight and the residual mixture was then filtered. The solvent was evaporated from the filtrate and the residual oil was distilled to yield 6-(4-pyridyl)-8-dimethylamino-3-oxaoctan-1-ol (30 gms, 40% conversion of starting material fed) b.p. 140°–148° C/1 mm Hg.

I.R. (liquid film) 3400, 2950, 2850, 2800, 2780, 1600, 1450, 1400, 1120, 1050, 1000 and 825 cm$^{-1}$ N.M.R. $\tau$(CCl$_4$) 1.6, 2.9, 5.5, 6.45, 6.65, 7.2, 7.95, 8.25 (Relative intensities 2:2:1:2:4:1:8:4)

M.S. M/$\epsilon$ 252.1835 (C$_{14}$H$_{24}$N$_2$O$_2$ has M/$\epsilon$ 252.1837)

EXAMPLE 17

To stirred liquid ammonia (2 liters) was added ferric nitrate (0.1 gm) followed by sodium metal (8.0 gms) in 1 gram pieces over a period of 20 minutes. To the resulting solution was added 3-(4-pyridyl)-1-dimethylamino-pentane (49 gms) over a period of 3 minutes and a deep yellow colour was allowed to develop over a period of 2 hours. Liquid ethylene oxide (14.6 gms) was then added and the mixture was stirred for a further 3 hours. Solid ammonium chloride (20 gms) was then added in small portions, followed by diethyl ether (1 liter). The ammonia was allowed to evaporate overnight and the residual mixture was filtered. The solvent was evaporated from the filtrate and the residual oil was distilled to yield 3-(4-pyridyl)-5-dimethylamino pentan-1-ol (32 gms, 46% conversion) b.p. 140°–146° C/0.5 mm Hg (m.p. 26° C).

I.R. (liquid film) 3400, 2950, 2850, 2800, 2780, 1600, 1450, 1400, 1050, 1000 and 825 cm$^{-1}$ N.M.R. $\tau$(CCl$_4$) 1.6, 2.9, 5.0, 6.7, 7.2, 7.95, 8.1 (Relative intensities 2:2:1:2:1:8:4)

M.S. M/$\epsilon$ 208.1585 (C$_{12}$H$_{20}$N$_{20}$ has M/$\epsilon$ 208/1575)

EXAMPLE 18

To stirred liquid ammonia (2 liters) was added ferric nitrate (0.1 gm) followed by potassium metal (20 gms) in 1 gram pieces over a period of 20 minutes. The resulting solution was added with stirring to a solution of (2-chloroethyl)-dimethylamine hydrochloride (72 gms) in liquid ammonia (1 liter). This solution was designated "Solution A".

To stirred liquid ammonia (2 liters) was added ferric nitrate (0.1 gm) followed by potassium metal (20 gms) in 1 gram pieces over a period of 20 minutes. To the resulting solution was added gamma-picoline (23 gms) over a period of 3 hours. The resulting solution was then added to Solution A and the resulting mixture was stirred for 3 hours. Solid ammonium chloride (60 gms) was then added, followed by ether (1 liter). The ammonia was allowed to evaporate overnight and the residual mixture was filtered. The solvent was evaporated from the filtrate and the residual oil was distilled to yield 3-(4-pyridyl)-1,5-bisdimethylaminopentane (23 gms, 40% conversion); b.p. 111°–120° C1 mm Hg.

I.R. (liquid film) 2950, 2850, 2780, 1600, 1460, 1410, 1040 and 830 cm$^{-1}$

N.M.R. $\tau$(CCl$_4$) 1.55, 2.9, 7.2, 7.9, 8.2 (Relative intensities 2:2:1:16:4)

M.S. M/$\epsilon$ 235.2044 (C$_{14}$H$_{25}$N$_3$ has M/$\epsilon$ 235.2048)

EXAMPLE 19

To stirred liquid ammonia (2 liters) was added ferric nitrate (0.1 gram) followed by sodium metal (4.6 gms) in 1 gram pieces over a period of 5 minutes. The resulting solution was allowed to stand for 20 minutes and 3-(4-pyridyl)-1-diethylaminopentane (38.4 gms) was added. A deep yellow colour was allowed to develop over a period of 3 hours. Solid ammonium chloride (20 gms) was added in small portions and the ammonia was allowed to evaporate overnight. The residual tacky oil was extracted into methylene chlorine, filtered and the solvent was evaporated from the filtrate. Distillation of the residual oil gave 3-(4-pyridyl)-5-diethylamino-pentan-1-ol (39 gms, 83% conversion) b.p. 175°–177° C/2.0 mm Hg.

I.R. (liquid film) 3400, 2950, 2850, 2800, 2780, 1600, 1400, 1360, 1050 and 820 cm$^{-1}$ N.M.R. $\tau$(CDCl$_3$) 1.55, 2.83, 4.75, 6.52, 7-8.5, 9.05 (Relative intensities 2:2:1:2:11:6)

M.S. M/$\epsilon$ 236.1885 (C$_{14}$H$_{24}$N$_2$O has M/$\epsilon$ 236.1888)

EXAMPLE 20

To stirred liquid ammonia (2 liters) was added ferric nitrate (0.1 gm) followed by potassium metal (20 gms) in 1 gram pieces over a period of 20 minutes. The resulting solution was added with stirring to a solution of 2-chlorotriethylamine hydrochloride (86 gms) in liquid ammonia (1 liter). This solution was designated "Solution A".

To stirred liquid ammonia (2 liters) was added ferric nitrate (0.1 gm) followed by potassium metal (20 gms) in 1 gram pieces over a period of 20 minutes. To the resulting solution was added gamma-picoline (23 gms) over a period of 3 minutes and a deep yellow colour was allowed to develop over a period of 2 hours. The resulting solution was added to Solution A and the resulting mixture was stirred for 3 hours. Solid ammonium chloride (60 gms) was then added followed by diethyl ether (1 liter). The ammonia was allowed to evaporate overnight and the residual mixture was filtered. The solvent was evaporated from the filtrate and the residual oil was distilled to yield 3-(4-pyridyl)-1,5-bisdiethylaminopentane (32 gms, 44% conversion) b.p. 153°–154° C/1.5 mm Hg. I.R. (liquid film) 2950, 2850, 2800, 2780, 1600, 1450, 1400, 1360, 1190, 1075, 1060 and 820 cm$^{-1}$ N.M.R. $\tau$(CCl$_4$) 1.65, 3.02, 7.30, 7.65, 7.85, 8.3, 9.1 (Relative intensities 2:2:1:8:4:3:2:12)

M.S. M/$\epsilon$ 291.2690 (C$_{18}$H$_{33}$N$_3$ has M/$\epsilon$ 291.2674)

EXAMPLE 21

To stirred liquid ammonia (2 liters) was added ferric nitrate (0.1 gm) followed by potassium metal (20 gms) in 1 gram pieces over a period of 20 minutes. To the resulting solution, gamma-picoline (23 gms) was added over a period of 3 minutes and a deep yellow colour was allowed to develop over a period of 2 hours. Vinyl chloroethyl ether (53 gms) was then added over a period of 30 minutes and the mixture was stirred for a further 5 hours. Solid ammonium chloride (25 gms) was then added in small portions followed by diethyl ether (1 liter). The ammonia was allowed to evaporate overnight and the residual mixture was filtered.

The solvent was evaporated from the filtrate and the residual oil was distilled to yield 6-(4-pyridyl)-3,9-dioxa-undeca-1,10-diene (59 gms, 50% conversion) b.p. 141°–143° C/1.5 mm Hg.

I.R. (liquid film) 3050, 2950, 2850, 1640, 1620, 1600, 1400, 1310, 1190, 990, 960 and 820 cm$^{-1}$ N.M.R. $\tau(CCl_4)$ 1.45, 2.85, 8.60, 6.0, 6.15, 6.5, 7.05, 8.05 (Relative intensities 2:2:2:2:2:4:1:4)

M.S. M/e 233.1421 ($C_{14}H_{19}NO_2$ has M/e 233.1416)

EXAMPLE 22

To stirred liquid ammonia (2 liters) was added ferric nitrate (0.1 gm) followed by potassium metal (20 gms) in 1 gram pieces over a period of 20 minutes. To the resulting solution gamma-picoline (46.6 gms) was added over a period of 3 minutes and a deep yellow colour was allowed to develop over a period of 2 hours. Vinyl chloroethyl ether (53 gms) was added as quickly as the exothermic reaction allowed and the mixture was stirred for a further 2 hours. Solid ammonium chloride (25 gms) was then added in small portions, followed by diethyl ether (1 liter). The ammonia was allowed to evaporate overnight and the residual mixture was filtered. The solvent was evaporated from the filtrate and the residual oil was distilled to yield vinyl 3-(4-pyridyl)-prop-1-yl ether (61 gms, 75% conversion); b.p. 90°–96° C/1 mm Hg.

I.R. (liquid film) 3050, 2950, 2850, 1640, 1620, 1600 1400, 1310, 1195, 990 and 820 cm$^{-1}$ N.M.R. $\tau(CCl_4)$ 1.55, 2.95, 3.53. 5.9, 6.05, 6.4, 7.35, 8.1 (Relative intensities 2:2:1:1:1:2:2:2)

M.S. M/e 163.0991 ($C_{10}H_{13}NO$ has M/e 163.0997)

The distillation residue was shown to contain 6-(4-pyridyl)-3,9-dioxa-undeca-1,10-diene.

EXAMPLE 23

To stirred liquid ammonia (2 liters) was added ferric nitrate (0.1 gm) followed by potassium metal (14 gms) in 1 gram pieces over a period of 20 minutes. To the resulting solution 3-(4-pyridyl)-propionaldehyde diethyl acetal (21 gms) was added over a period of 3 minutes and a deep yellow colour was allowed to develop over a period of 2 hours. Liquid ethylene oxide (25 mls) was then added and the mixture was stirred for a further 3 hours. Solid ammonium chloride (20 gms) was added in small portions followed by diethyl ether (1 liter). The ammonia was allowed to evaporate overnight and the residual mixture was filtered. The solvent was evaporated from the filtrate and the residual oil was distilled to give 1,1-diethoxy-3-(4-pyridyl)-pentan-5-ol (18 gms, 70% conversion) b.p. 170°–175° C/1 mm Hg, as a thick colourless oil.

I.R. (liquid film) 3400, 2950, 2850, 1600, 1400, 1130, 1055 and 1000 cm$^{-1}$

N.M.R. $\tau(CCl_4)$ 1.55, 2.85, 5.55, 5.85, 6.6, 7.05, 8.2, 8.85 (Relative intensities 2:2:1:1:6:1:4:6)

M.S. M/e 253.1671 ($C_{14}H_{23}NO_3$ has M/e 263.1677)

EXAMPLE 24

To a stirred suspension of sodamide (3.9 gms) in 3-(4-pyridyl)-propionaldehyde diethyl acetal (20.0 gms) was added dropwise, under nitrogen, chloroacetal (15.2 gms) at such a rate that the temperature did not exceed 30° C. The mixture was allowed to stand for 20 hours after which time saturated aqueous ammonium chloride was added dropwise until no further reaction occurred. The organic layer was separated and the aqueous phase was extracted several times into diethyl ether. The organic extracts were combined and dried and the solvent was evaporated. Distillation of the residual oil yielded starting pyridylpropionaldehyde acetal (13 gms, 65% recovery) and a fraction (6 gms, 12% conversion) identified from its spectra as 3-(4-pyridyl)-glutaraldehyde tetraethyl acetal; b.p. 149°–154° C/1 mm Hg.

I.R. (liquid film) 3020, 2950, 2850, 1600, 1420, 1370, 1150, 1130, 1065 and 1000 cm$^{-1}$ N.M.R. $\tau(CCl_4)$ 1.55, 2.9, 5.7, 6.6, 7.2, 8.15, 8.9 (Relative intensities 2:2:2:8:1:4:12)

M.S. M/e 325.2240 ($C_{18}H_{31}NO_4$ has M/e 325.2252)

EXAMPLE 25

To stirred liquid ammonia (2 liters) was added ferric nitrate (0.1 gm) followed by sodium metal (2.3 gms) in small pieces. The mixture was allowed to stand for 30 minutes and 3-(4-pyridyl)-propionaldehyde diethyl acetal (20.0 gms) was then added. A deep yellow colour was allowed to develop over a period of 2 hours, after which time ethylene sulphide (6.0 gms) was added quickly. A vigorous reaction occurred and the mixture was stirred for a further 5 hours. Ammonium chloride (7 gms) was added and the solvent was allowed to evaporate overnight. The residual tacky solid was extracted into pyridine and filtered and the solvent was evaporated from the filtrate. Distillation of the residual oil yielded 3-(4-pyridyl)-5,5-diethoxy-pentane-1-thiol (17 gms, 63% conversion) b.p. 167°–172° C/1 mm Hg, characterised by the following spectra:

I.R. $\nu$max (liquid film) 2950, 2850, 2550, 1600, 1400, 1120, 1050, 990 and 820 cm$^{-1}$ M.S. M/e 269.1469 weak ($C_{14}H_{23}NO_2S$ has M/e 269.1449), 223.1033 ($C_{12}H_{17}NOS$ has M/e 223.1031) and 103.0760 $C_5H_{11}O_2$ has M/e 103.0758)

N.M.R. $\tau(CCl_4)$ 1.55, 2.9, 5.9, 6.6, 7.15, 7.8, 8.15 (Relative intensities 2:2:1:4:1:2:4:1:6)

EXAMPLE 26

To stirred liquid ammonia (2 liters) was added ferric nitrate (0.1 gm) followed by sodium metal (6.3 gms) in small pieces. The mixture was allowed to stand for 30 minutes and 3-(4-pyridyl)-propan-1ol (19 gms) was then added. A deep yellow colour was allowed to develop over a period of 2 hours after which time ethylene sulphide (8.3 gms) was added quickly. A vigorous reaction occurred and the mixture was stirred for a further 4 hours. Ammonium chloride (10 gms) was added and the solvent was allowed to evaporate overnight. The residual tacky solid was extracted into pyridine and the mixture was filtered and the solvent evaporated. Distillation of the residual oil yielded 3-(4-pyridyl)-5-hydroxy-pentane-1-thiol (12.7 gms, 60% conversion); b.p. 177°–185° C/1 mm Hg, m.p. 50°–52° C, characterised by the following spectra:

I.R. $\nu$max (melt) 3350, 2950, 2850, 2550, 1600, 1400, 1950, 1000 and 820 cm$^{-1}$ M.S. M/e 197.0974 ($C_{10}H_{15}NOS$ has M/e 197.0873)

N.M.R. $\tau((CD_3)_2CO)$ 1.4, 2.65, 7–8.5 (Relative intensities 2:2:11)

EXAMPLE 27

To stirred liquid ammonia (2 liters) was added ferric nitrate (0.1 gm) followed by sodium metal (2.3 gms) in small pieces. The mixture was allowed to stand for 30 minutes and 3-(4-pyridyl)-1-diethylamino propane (19.2 gms) was then added. A deep yellow colour was allowed to develop over a period of 2 hours, after which time ethylene sulphide (6.0 gms) was added quickly. A vigorous reaction occurred and the mixture was stirred for a further 5 hours. Ammonium chloride (7 gms) was added, and the solvent was allowed to evaporate overnight. The residual tacky solid was extracted into pyridine and the extract was filtered and the solvent evaporated. Distillation of the residual oil-yielded 3-(4-pyridyl)-5-diethylamino-pentane-1-thiol, (18 gms, 72% conversion) b.p. 140°–143° C/0.2 mm Hg, characterised by the following spectra:

I.R. $\nu$max (liquid film) 2950, 2850, 2760, 2500, 1600, 1400, 1060, 990 and 820 cm$^{-1}$ M.S. M/$\epsilon$ 252.1652 ($C_{14}H_{24}N_2S$ has M/$\epsilon$ 252.1652)

N.M.R. $\tau$(CCl$_4$ + CDCl$_3$) 1.45, 2.9, 7.2, 7.6, 7.7, 8.1, 9.1 (Relative intensities 2:2:1:4:4:5:6)

EXAMPLE 28

To stirred liquid ammonia (300 mls) was added ferric nitrate (50 mgs) followed by sodium metal (4.5 gms). The mixture was allowed to stand for 30 minutes and then 3-(4-pyridyl)-1-amino propane (13.5 gms) was added. A deep yellow colour was allowed to develop over 1 hour and ethylene oxide (5.0 gms) was then added. The mixture was stirred for a further 2 hours after which time solid ammonium chloride (12 gms) was added. The solvent was allowed to evaporate overnight and the residual solid was extracted into pyridine. Evaporation of the pyridine and crystallisation of the residue from benzene yielded 3-(4-pyridyl)-1-amino-5-hydroxy pentane (3.4 gms; 17%). Characterised by the following spectral data:

I.R. $\nu$ max (nujol mull) 3300, 2950, 2850, 1600, 1400, 1050, 990, 820 and 710 cm$^{-1}$ M.S. M/$\epsilon$ 180.1259 ($C_{10}H_{16}N_2O$ has M/$\epsilon$ 180.1262)

EXAMPLE 29

To stirred liquid ammonia (300 mls) was added ferric nitrate (50 mgs) followed by sodium metal (7.0 gms). The mixture was allowed to stand for 30 minutes and then 3-(4-pyridyl)-propan-1-ol (13.7 gms) in diethyl ether (25 mls) was added. A deep yellow colour was allowed to develop over 1 hour and chloracetamide (10.7 gms) was then added slowly over 2 hours. The reaction was stirred for a further 2 hours after which time solid ammonium chloride (18 gms) was added. The solvents were allowed to evaporate overnight and the residual solid was extracted into pyridine. Evaporation of the pyridine and recrystallisation of the residual solid from water yielded 2-(4-pyridyl)-1-amido-4-hydroxy butane (4.5 gms; 30%(, characterised by the following spectral data.

M.S. M/$\epsilon$ = 194.1063 ($C_{10}H_{14}N_2O_2$ has M/$\epsilon$ = 194.1055)

EXAMPLE 30

To stirred liquid ammonia (1 liter) was added ferric nitrate (0.1 gm) followed by sodium metal (12.0 gms) in 1 gram pieces over a period of 30 minutes. To the resulting solution alpha-picoline (23.3 gms) was added followed by 4-chloro butyl acetate (37.5 gms). The mixture was stirred for 4 hours after which time ammonium chloride (30 gms) was added in small pieces.

The solvent was allowed to evaporate and the residue was extracted into diethyl ether, washed with dilute hydrochloric acid, and the extracts were made alkaline. These were then extracted into diethyl ether and dried, and the solvent was evaporated. The residual oil was allowed to stand for 4 days with acetic anhydride (40 ml) and pyridine (40 ml), the solvents were then evaporated. The residue was poured into water, neutralised with potassium carbonate and extracted into diethyl ether. The extracts were dried, the solvent was evaporated, and the residual oil was distilled to yield 5-(2-pyridyl)-pentan-1-yl acetate b.p. 120°–123° C/1 mm Hg (15 gms; 34%), identified by the following spectral data:

I.R. (liquid film) 2950, 1740, 1580, 1470, 1440, 1240, 1050, and 760 cm$^{-1}$

N.M.R. $\tau$(CCl$_4$) 1.7, 2.6, 3.1, 6.1, 7.4, 8.15 and 8.5 (Relative intensities 1:1:2:2:2:3:6)

M.S. M/$\epsilon$ = 207.1251 ($C_{12}H_{17}NO_2$ has M/$\epsilon$ = 207.1259)

EXAMPLE 31

Aqueous hydrogen peroxide (13 mls of 30% solution) was added over 2 hours to a solution of 5-(2-pyridyl)-pentan-1-yl acetate (13.0 gms) in acetic acid (50 mls) at 75° C. After 16 hours and mixture was heated to 95° C and paraformaldehyde (1.8 gms) was added. After a further 2 hours the solvent was evaporated in vacuo and the residual oil was added to acetic anhydride (50 mls) and heated at 95° C for 6 hours. The solvent was evaporated and the product was poured onto ice, neutralised with potassium carbonate and extracted into diethyl ether. Evaporation of the ether and distillation of the residual oil yielded 1-(2-pyridyl)-1,5-diacetoxy pentane, b.p. 140°–141° C/1 mm (8 gms; 40%). Characterised by the following spectral data:

I.R. (liquid film) 2950, 1750, 1580, 1470, 1430, 1370, 1240, 1200 and 1050 cm$^{-1}$ N.M.R. $\tau$(CDCl$_3$) 1.35, 2.3, 2.75, 4.1, 5.9, 7.85, 8.0 and 8.4 (Relative Intensities 1:1:2:1:2:3:3:6)

M.S. M/$\epsilon$ = 265.1310 ($C_{14}H_{19}NO_4$ has M/$\epsilon$ = 265.1314)

EXAMPLE 32

1,5-diacetoxy-1-(2-pyridyl)-pentane (3.0 gms) was suspended in 10% sodium hydroxide solution and the mixture was stirred at room temperature for 3 days. The residue was washed with methylene chloride and extracted into butanol. The butanol extracts were evaporated to dryness to leave a waxy solid (1.2 gms; 56%) identified as 1-(2-pyridyl)-pentane-1,5-diol by the following spectral data:

I.R. (liquid film) 3300, 2950, 2850, 1580, 1560, 1470, 1430, 1280, 1070 and 1020 cm$^{-1}$ M.S. M/$\epsilon$ = 181.1108 ($C_{10}H_{15}NO_2$ has M/$\epsilon$ = 181.1102)

EXAMPLE 33

A solution of benzoyl peroxide (50 mgs) and redistilled 4-(4-pyridyl)-tetrahydropyran (5.0 gms) in dry carbon tetrachloride (50 mls) was added to powdered N-bromosuccinimide (5.5 gms) and the mixture was heated under reflux for 2 hours. A thick red-brown oil separated. The product was cooled to 0° C for 16 hours and filtered, and the filtrate was evaporated almost to dryness. The product was isolated by chromatography on alumina using carbon tetrachloride/1% methanol as solvent. The product (3 gms) was recrystalised from carbon tetrachloride as unstable white tablets characterised by the following data:

m.p. 77–78° C

I.R. (CCl$_4$) 1590, 1395, 1150, 1100, 1040, 1025, 920 + 780 cm$^{-1}$

N.M.R. $\tau$ (CCl$_4$) 1.4, 2.65, 6.15, 7.8 (Relative Intensities 2:2:4:4)

M.S. M/$\epsilon$ = 241.0092 (C$_{10}$H$_{12}$BrNO has M/$\epsilon$ = 241.0102), 162.0918, 161

EXAMPLE 34

Aqueous hydrogen peroxide (21 mls of 30% solution) was added over 2 hours to a solution of 4-(4-pyridyl)-tetrahydropyran (16.0 gms) in acetic acid (18 mls) at 75° C. After 20 hours the mixture was heated to 95° C and paraformaldehyde (2.0 gms) was added. After 2 hours the solvent was evaporated in vacuo and the residual oil was added to acetic anhydride (60 mls) at 100° C. The product was poured onto ice and made slightly alkaline with potassium hydroxide solution. After 6 hours the product was extracted into diethyl ether, and after removal of the solvent, the product was recrystallised from carbon tetrachloride as white blocks m.p. 154° C characterised by the following spectral data:

I.R. (nujol mull) 3250, 1600, 1380, 1140, 1120, 1080, 1010, 840 and 830 cm$^{-1}$ N.M.R. $\tau$ (CDCl$_3$, 60°) 1.55, 2.55, 6.15, 6.55, 7.8–8.5 (Relative intensities 2:2:4:1:4)

M.S. M/$\epsilon$ = 179.0956 (C$_{10}$H$_{13}$NO$_2$ has M/$\epsilon$ = 179.0946)

EXAMPLES 35 to 87

These examples illustrate the conversion of substituted pyridines into bipyridyls.

The experimental procedure in each example was as follows:

A catalyst bed was prepared from a pelleted form of the catalyst (see below) to the specified depth in a vertical glass reactor tube of internal diameter 1 inch. The tube was fitted with a central thermocouple pocket and contained Raschig rings above the catalyst bed. The Raschig rings did not completely fill the tube. The tube was positioned in a vertical furnace maintained at the appropriate temperature.

The substituted pyridine was dissolved in water or methanol or (Example 72) pyridine and the solution was fed to the top of the reactor tube where it was vaporised on contact with the Raschig rings. The vapours were passed downwardly through the catalyst bed. The vapours were mixed with oxygen, nitrogen or ammonia as indicated in the Table for passage through the catalyst bed, although in a few cases mixing was carried out below the surface of the catalyst bed.

The reactor effluent was condensed and the condensate if liquid (as in the majority of the experiments) was analysed by gas/liquid chromatography using standard techniques. Where the condensate was a solid this was dissolved in methanol and the solution was analysed.

In the Table the catalyst is designated by a reference letter A, B, C or D:

A. ⅛ × ⅛ pelleted alumina (Actal 'A')
B. activated copper oxide/chromia (I.C.I. 26-3)
C. 0.5% platinum on 50% alumina/50% silica-alumina
D. 13% alumina silica + alumina (Crosfield - Grade 77)

In the Table also:

'Bipyridyl' means 4,4'-bypyridyl unless otherwise stated
'Length' is the length of the catalyst bed
'Temp.' is the temperature of the catalyst bed
'dilution' is in terms of gms starting material/mls solvent
'MeOH' is methanol

TABLE

| Ex. No. | Substituted pyridine | Catalyst | Bed Length (ins.) | Temp. (° C) | Time (mins.) | Dilution | Solvent | Air | N$_2$ | NH$_3$ | 4,4'-bipyridyl (conversion percent) |
|---|---|---|---|---|---|---|---|---|---|---|---|
| 35 | 3-(4-pyridyl)-1,1-diethoxy-5-dimethylamino pentane. | A | 3 | 360–420 | 51 | 1.3/20 | MeOH | 100 | — | 830 | 57 |
| 36 | 6-(4-pyridyl)-8-dimethylamino-3-oxaoctan-1-ol. | A | 3 | 350–390 | 100 | 2.6/50 | H$_2$O/MeOH (2:1) | 100 | — | 830 | 72 |
| 37 | 3-(4-pyridyl)-5-dimethylamino-pentan-1-ol. | A | 3 | 330–360 | 50 | 4.5/30 | MeOH | 100 | — | 830 | 41 |
| 38 | 3-(4-pyridyl)-1,5 bis-dimethyl-amino pentane. | A | 3 | 320–340 | 47 | 2.4/25 | MeOH | 100 | — | 830 | 39 |
| 39 | 3-(4-pyridyl)-5-diethylamino-pentan-1-ol | A | 3 | 330–363 | 70 | 4.7/18 | MeOH | 100 | — | 830 | 36 |
| 40 | 3-(4-pyridyl)-1,5 bis-diethylamino pentane. | A | 3 | 320–380 | 60 | 3.3/30 | MeOH | 100 | — | 830 | 34 |
| 41 | 6-(4-pyridyl)-3,9-dioxa-undeca-1,10-diene. | A | 3 | 375–401 | 66 | 2.3/25 | MeOH | 100 | — | 830 | 26 |
| 42 | 3-(4-pyridyl)-1,1-diethoxy-pentan-5-ol. | A | 3 | 340–360 | 45 | 3.5/25 | MeOH | 100 | — | 830 | 24 |
| 43 | " | A | 3 | 350–380 | 45 | 3.0/25 | H$_2$O/MeOH (1:1) | 100 | — | 830 | 39 |
| 44 | 3-(4-pyridyl)-glutaraldehyde tetra-ethyl acetal. | A | 3 | 350–390 | 60 | 2.66/25 | MeOH | 100 | — | 830 | 86 |
| 45 | 3-(4-pyridyl)-glutaraldehyde tetra-ethyl acetal. | A | 3 | 370–390 | 77 | 1.85/25 | H$_2$O/MeOH (50:50) | 100 | — | 830 | 70 |
| 46 | 3-(4-pyridyl)-5,5-diethoxy-pentane-1-thiol. | A | 3 | 360–400 | 52 | 1.82/25 | MeOH | 100 | — | 830 | 58 |
| 47 | 3-(4-pyridyl)-5-hydroxy-pentane-1-thiol. | A | 3 | 380–415 | 75 | 2.1/25 | MeOH | 100 | — | 830 | 19 |
| 48 | 3-(4-pyridyl)-5-diethylamino-pentane-1-thiol. | A | 3 | 365–410 | 70 | 1.26/25 | MeOH | 100 | — | 830 | 64 |
| 49 | 3-(4-pyridyl)-pentane-1,5-dithiol | A | 3 | 350–400 | 67 | 1.3/25 | MeOH | 100 | — | 830 | 8 |
| 50 | 2-(2-pyridyl)-tetrahydropyran | A | 3 | 380–420 | 34 | 1.1/25 | MeOH | 100 | — | 830 | $^1$13 |
| 51 | 4-(4-pyridyl)-tetrahydropyran | A | 3 | 370 | 30 | 2.1/10 | H$_2$O | 50 | — | 500 | 20 |
| 52 | " | A | 3 | 370 | 35 | 2.5/12.5 | H$_2$O | — | — | 500 | 6 |
| 53 | " | A | 3 | 370 | 56 | 4.5/25 | MeOH | 100 | — | 830 | 15 |
| 54 | " | A | 2½ | 340–360 | 50 | 2.9/16.3 | H$_2$O | 50 | — | 300 | 10 |
| 55 | " | B | 3 | 360–370 | 60 | 4.4/25 | MeOH | 100 | — | 830 | 9 |
| 56 | " | B | 3 | 360–370 | 60 | 4.4/25 | MeOH | — | 100 | 830 | 11 |
| 57 | 3-(2-pyridyl)-pentane-1,5-diol | A | 3 | 360–380 | 60 | 3.6/18 | MeOH | 100 | — | 830 | $^2$10 |

TABLE -continued

| Ex. No. | Substituted pyridine | Catalyst | Bed Length (ins.) | Temp. (° C) | Time (mins.) | Liquid feed Dilution | Solvent | Gas feeds (ml./min.) Air | N₂ | NH₃ | 4,4'-bipyridyl (conversion percent) |
|---|---|---|---|---|---|---|---|---|---|---|---|
| 58 | " | B | 3½ | 340–360 | 120 | 15/75 | MeOH | — | 830 | ²22 | |
|   |   |   |   |   |   | MeOH |   |   |   |   |   |
| 59 | 3-(3-pyridyl)-pentane-1,5-diol | A | 4 | 370–400 | 60 | 5/25 | MeOH | 100 | — | 830 | ³10 |
| 60 | " | B | 3 | 370–390 | 120 | 1.95/25 | MeOH | 100 | — | 830 | ³18 |
| 61 | 3-(4-pyridyl)-pentane-1,5-diol | C | ⁵4 | 360–380 | 50 | 4.8/25 | MeOH | 100 | 67 | 830 | 46 |
| 62 | " | B | ⁵6 | 360–364 | 50 | 5/25 | MeOH | 100 | 100 | 830 | 75 |
| 63 | " | A | 4 | 400 | 50 | 2.6/18 | H₂O | — | 100 | 500 | 8 |
| 64 | " | A | 3 | 400 | 180 | 15/75 | MeOH | 100 | — | 830 | 20 |
| 65 | " | A | 3 | 400 | 80 | 3.8/19 | H₂O | 100 | — | 500 | 20 |
| 66 | " | A | ⁵6½ | 300–340 | 66 | 5/26 | MeOH | 135 | 60 | 830 | 30 |
| 67 | " | D | ⁵3+3 | 325–375 | 59 | 6.4/25 | MeOH | 100 | 100 | 830 | 16 |
| 68 | " | D | ⁵3+3 | 330–370 | 51 | 5/25 | MeOH | 100 | 300 | 830 | 13 |
| 69 | " | A | 6 | 320–380 | 82 | 5/25 | MeOH | 100 | — | 830 | 26 |
| 70 | " | A | 3 | ⁶350–390 | ⁷11 | 51.4/260 | MeOH | 100 | — | 830 | 18 |
| 71 | " | D | 3 | 320–380 | 30 | 8.6/43 | H₂O | 100 | — | 500 | 12 |
| 72 | " | A | 3 | 370–400 | 30 | 1.8/39 | Pyridine | 60 | — | 500 | 5 |
| 73 | " | B | ⁵6 | 360–380 | ⁷7 | 35/125 | MeOH | 100 | 100 | 830 | 60 |
| 74 | " | B | ⁵6 | 360–380 | 100 | 10/50 | MeOH | — | 60 | 830 | 67 |
| 75 | " | B | ⁵6 | 360–380 | 40 | 5/25 | MeOH | 35 | 60 | 830 | 84 |
| 76 | " | B | ⁵6 | 360–390 | 42 | 2.5/25 | H₂O | 100 | 67 | 830 | 17 |
| 77 | 3-(4-pyridyl)-glutaric acid diethyl ester. | A | 3 | 340–380 | 60 | 5.1/25 | MeOH | 100 | — | 830 | 3 |
| 78 | Ethyl 3-(4-pyridyl)-3[bis(carbethoxy) methyl]-propionate. | A | 3 | 360–380 | 45 | 10.1/75 | MeOH | 100 | — | 830 | 5 |
| 79 | 1-(2-pyridyl)-pentane-1,5-diol | B | 3 | 330–360 | 75 | 1.2/25 | MeOH | 100 | — | 830 | ¹18 |
| 80 | 1-(2-pyridyl)-1,5 diacetoxy-pentane | A | 3 | 350–380 | 45 | 1.0/25 | MeOH | 100 | — | 830 | ¹6 |
| 81 | 4-(4-pyridyl)-4-hydroxy tetrahydropyran. | A | 1 | 360–380 | 130 | 0.4/50 | MeOH | 100 | — | 830 | 10 |
| 82 | 4-(4-pyridyl)-4-bromo tetrahydropyran. | A | 1½ | 370–380 | 65 | 1.2/25 | MeOH | 100 | — | 830 | 5 |
| 83 | 4-(4-pyridyl)-piperidine | A | 3 | 340–405 | 70 | 2.08/25 | MeOH | 100 | — | 830 | 89 |
| 84 | 2-(3-pyridyl)-piperidine (Anabasine) | A | 3 | 337–401 | 52 | 1.9/25 | H₂O/MeOH (1:1) | 100 | — | 830 | ⁴72 |
| 85 | 4,4'-bipiperidyl-3-(4-pyridyl)-5-diethylamino-pentan-1-ol. | A | 3 | 370–415 | 30 | 4.7/18 | MeOH | 400 | 400 | — | 15 |

¹2,2'-bipyridyl.
²2,4-bipyridyl.
³3,4-bipyridyl.
⁴2,3-bipyridyl.
⁵In 1½" bore reactor.
⁶Mainly 370.
⁷Hours.

In the above Table the product listed is the major reaction product. However, in many examples the products were identified as follows:

| Example No. | Other Products |
|---|---|
| 37 | (4,4-pyridyl)-tetrahydropyran (19%) |
| 38 | (N-methyl-4-(4-pyridyl) piperidine |
| 39 | N-methyl-4-(4-pyridyl) piperidine |
|   | (4-(4-pyridyl)-tetrahydropyran |
|   | (N-ethyl-4-(4-pyridyl) piperidine |
| 40 | N-ethyl-4-(4-pyridyl) piperidine |
| 41, 46, 47, 48, 49, 61 to 76 | 4-(4-pyridyl)-tetrahydropyran |
| 57, 58 | 4-(2-pyridyl)-tetrahydropyran |
| 59, 60 | (4-(3-pyridyl)-tetrahydropyran |
|   | (3'-methyl-3,4'-bipyridyl |
| 84 | (2'- or 3'-methyl-2,3'-bipyridyl |
|   | (5-methyl-2,3'-bipyridyl |
| 85 | 4-(4-pyridyl)-piperidine |

N-ethyl 4(4-pyridyl)-piperidine

I.R. ν max (CCl₄) 3000, 2800, 2780, 1600, 1440, 1400, 1370 and 1130 cm⁻¹

N.M.R. τ [(ch₃)₂CO]1.5, 2.85, 7.1, 7.6-8.4, 8.98 (Relative intensities 2:2:1:10:3)

M.S. M/ε = 190.1469 (C₁₂H₁₈N₂ has M/ε = 190.1470)

The majority of the products (including those referred to as "other products") in Examples 35 to 87 were identified by comparison with authentic reference compounds. Those which could not be so identified were subjected to fractional distillation or to gas/liquid chromatographic analysis and their spectral data is given below:

3,4'-Bipyridyl

I.R. ν max (liquid film) 3050, 2950, 1600, 1580, 1465, 1420, 1400, 1025, 1015, 900, 840, 800, 765 and 715 cm⁻¹

N.M.R. τ (CCl₄) 1.28, 1.50, 1.69, 2.26, 2.66, 2.76 (Relative intensities 1:2:1:1:2:1)

M.S. $_εM$ = 156.0684 (C₁₀H₈N₂ has $_εM$ = 156.0687)

The compound gave a bright buttercup yellow colour with zinc dust/acetic acid.

3'-Methyl 3,4'-Bipyridyl

I.R. ν max (liquid film) 3050, 2950, 1600, 1530, 1450, 1440, 1400, 1020, 835, 820, 805, 750, 740 and 720 cm⁻¹

N.M.R. τ (CCl₄) 1.4–1.7, 2.45, 2.7, 2.95, 7.72 (Relative intensities 4:1:1:1:3)

M.S. $_εM$ = 170.0843 (C₁₁H₁₀N₂ has $_εM$ = 170.0843)

A Methyl-2,3'-bipyridyl (either 2'- or 3'-methyl-2,3'bipyridyl — characterization incomplete)

I.R. ν max (liquid film) 3020, 1585, 1575, 1405, 1010, 790, 770, 760, 710 cm⁻¹

M.S. 170.0833 (C₁₁H₁₀N₂ has $_εM$ = 170.0843)

5-Methyl-2,3'-bipyridyl

I.R. $\nu$ max (nujol mull) 15.75, 1420, 1030, 1020, 840, 810, 775, 760 and 710 cm$^{-1}$ N.M.R. $\tau$ (CCl$_4$) 0.75, 1.4, 1.6, 2.28, 2.42, 2.62, 7.6 (Relative intensities 1:2:1:1:1:1:3)

M.S. $_eM = 170.0833$ (C$_{11}$H$_{10}$N$_2$ has $_eM = 170.0843$)

What we claim is:

1. A compound selected from the group consisting of 4-(4'-pyridyl)-tetrahydropyran, 2-(2'-pyridyl)-tetrahydropyran, 4-(2'-pyridyl)-tetrahydropyran, and 4-(3'-pyridyl)-tetrahydropyran.

2. The compound 4-(4'-pyridyl)-tetrahydropyran.

3. A process for the manufacture of a 4-(pyridyl)tetrahydropyran which consists essentially of reacting a 2'-haloethyl-3-(pyridyl)propyl ether respectively, at $-80°$ C to $40°$ C with an alkali metal amide.

4. A process as claimed in claim 3 wherein the temperature is from $-80°$ C to $-10°$ C.

5. A process as claimed in claim 4 wherein the reaction is carried out in liquid ammonia.

6. A process as claimed in claim 3 wherein sodamide is employed.

7. A process as claimed in claim 3 wherein a 2'-chloroethyl-3(pyridyl) propyl ether, is employed.

* * * * *